US005611451A

United States Patent [19]
Mosior et al.

[11] Patent Number: 5,611,451
[45] Date of Patent: Mar. 18, 1997

[54] DISPOSAL CONTAINER WITH LOCKING CLOSURE AND INDICATOR TO PROVIDE VISUAL INDICATION OF LOCKING OF CLOSURE

[75] Inventors: Donald J. Mosior, Lake Geneva, Wis.; Edward C. Hay, Crystal Lake, Ill.

[73] Assignee: Sage Products, Inc., Crystal Lake, Ill.

[21] Appl. No.: 522,134

[22] Filed: Aug. 31, 1995

Related U.S. Application Data

[63] Continuation-in-part of Ser. No. 131,652, Oct. 5, 1993, Pat. No. 5,507,408.

[51] Int. Cl.$^6$ .................................................. B65D 43/20
[52] U.S. Cl. ......................... 220/346; 220/254; 220/329
[58] Field of Search .................................. 210/214, 254, 210/281, 282, 256, 297, 298, 329, 345, 346, 351, 354, 355, 356, 377, 293

[56] References Cited

U.S. PATENT DOCUMENTS

| | | | |
|---|---|---|---|
| 2,868,360 | 1/1959 | Donkin | 220/345 |
| 2,959,317 | 11/1960 | Aldridge | 220/345 |
| 3,942,630 | 3/1976 | Phillips | 220/329 |
| 4,127,212 | 11/1978 | Waterbury | 220/254 |
| 4,434,906 | 3/1984 | Florczyk et al. | 220/345 |
| 4,570,817 | 2/1986 | Hambleton et al. | 220/345 |

Primary Examiner—David Scherbel
Assistant Examiner—Tony G. Soohoo
Attorney, Agent, or Firm—Lee, Mann, Smith, McWilliams, Sweeney & Ohlson

[57] ABSTRACT

A disposal container including a lid having an access aperture, and a closure which is shaped to overlay and seal the access aperture. The closure is slidable in an operative position at a first elevation from a temporarily closed orientation over the access aperture to an opened orientation where at least a portion of the aperture is exposed. The closure can be locked in place over the access aperture by rotating the closure to align tabs on the closure with recesses in the lid, and then pushing the closure downwardly to a second elevation to lock it in place.

20 Claims, 9 Drawing Sheets

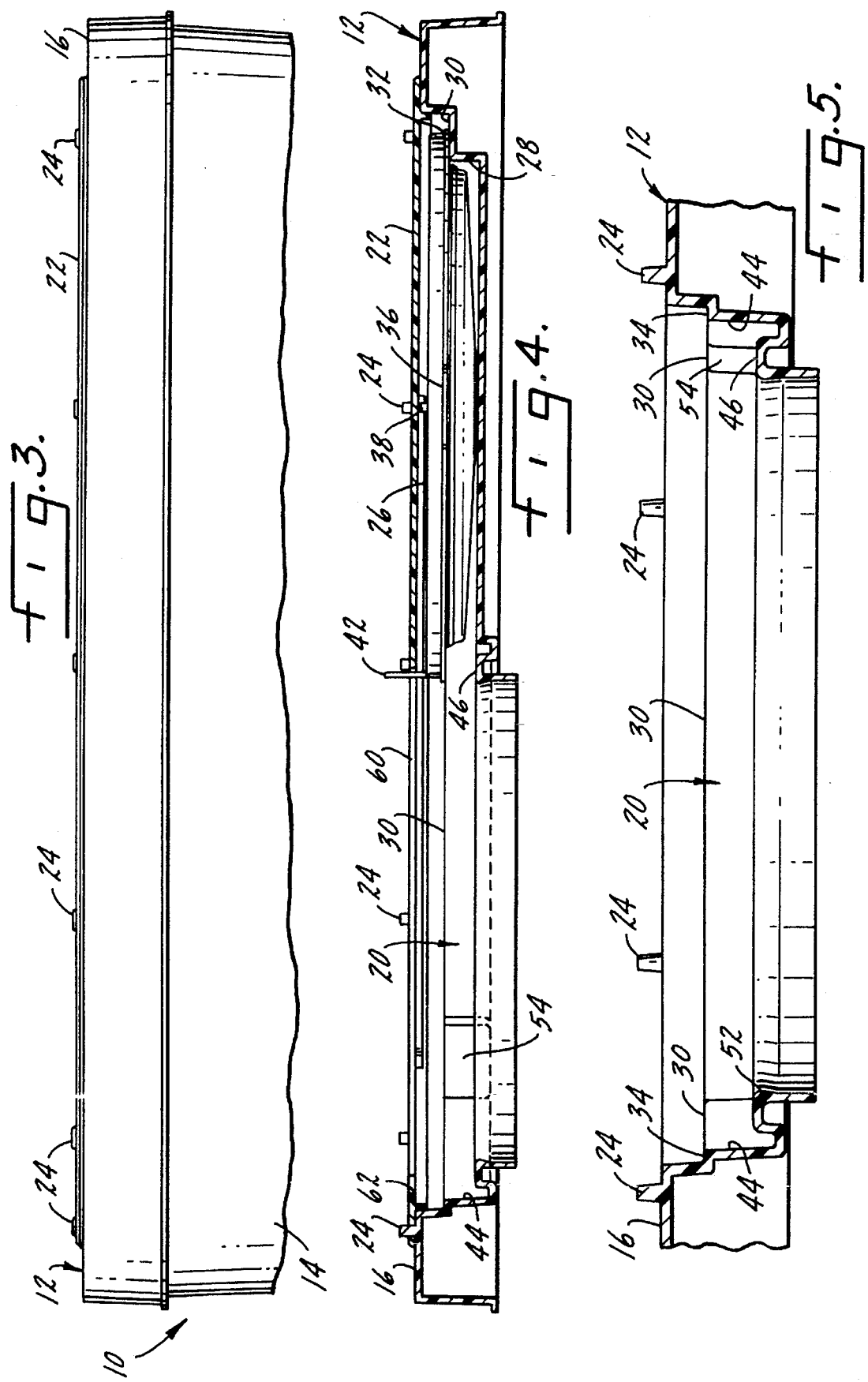

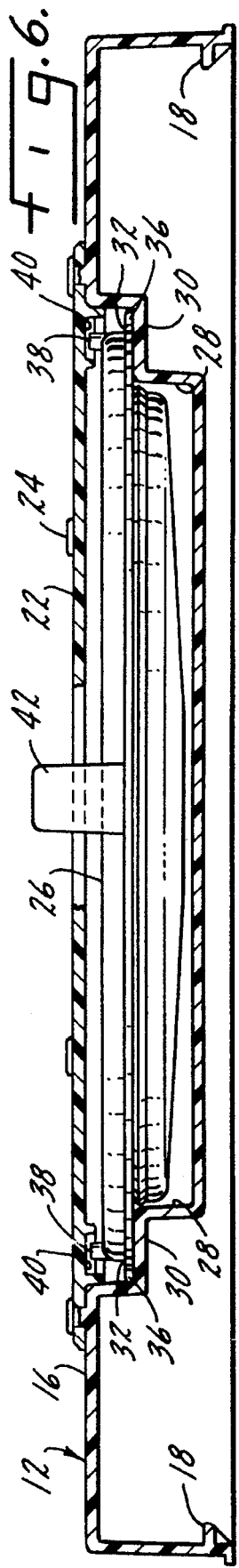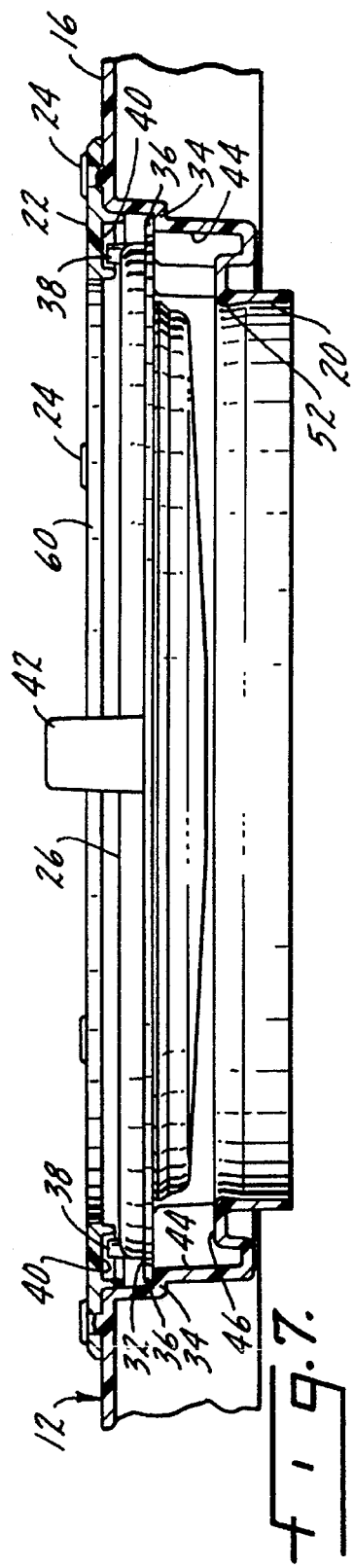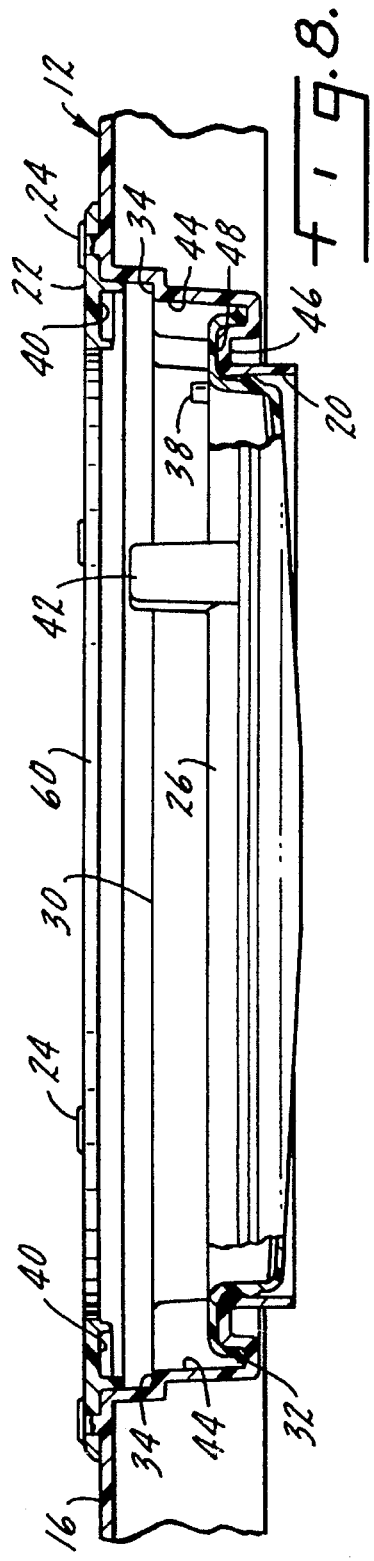

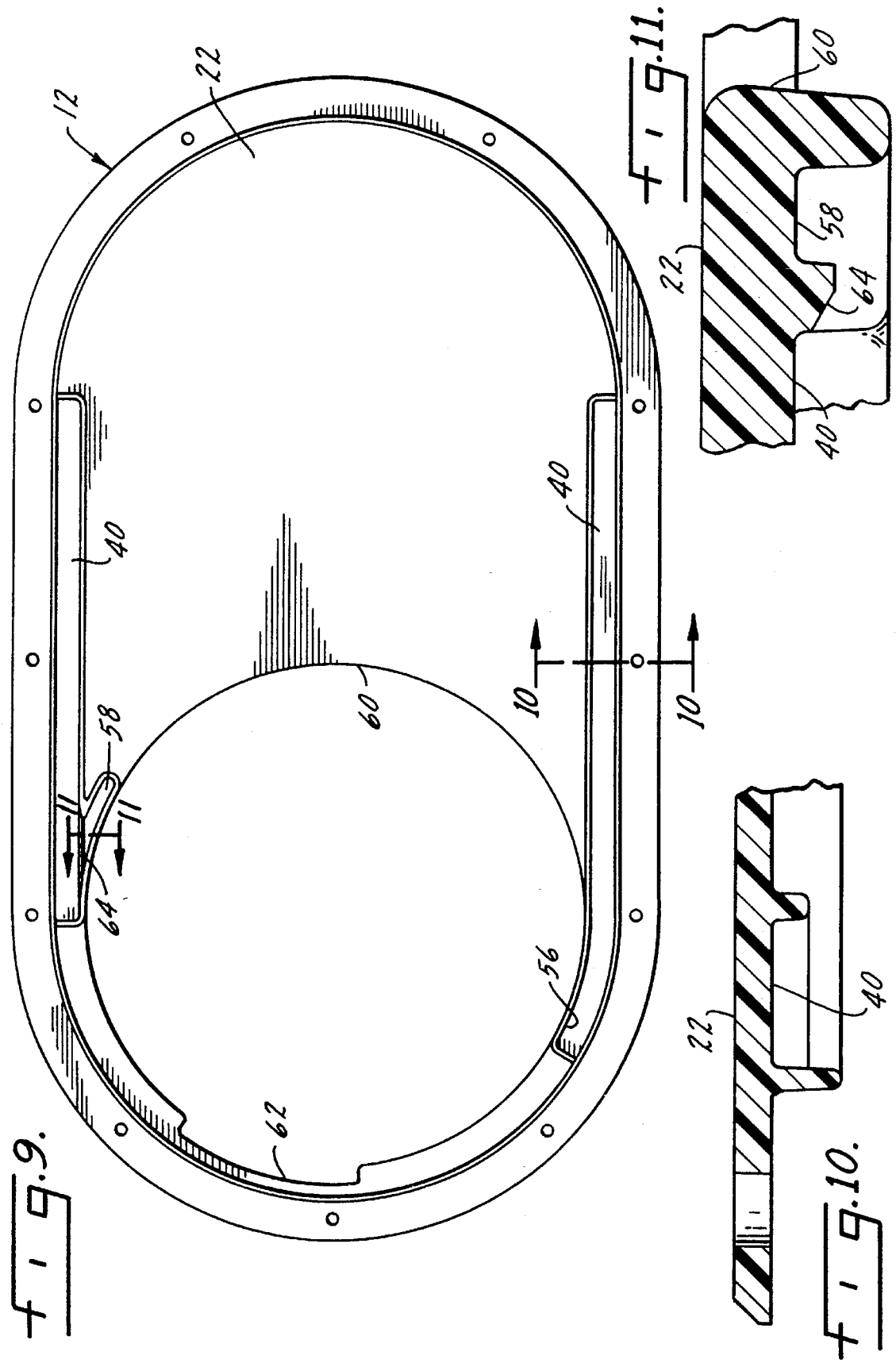

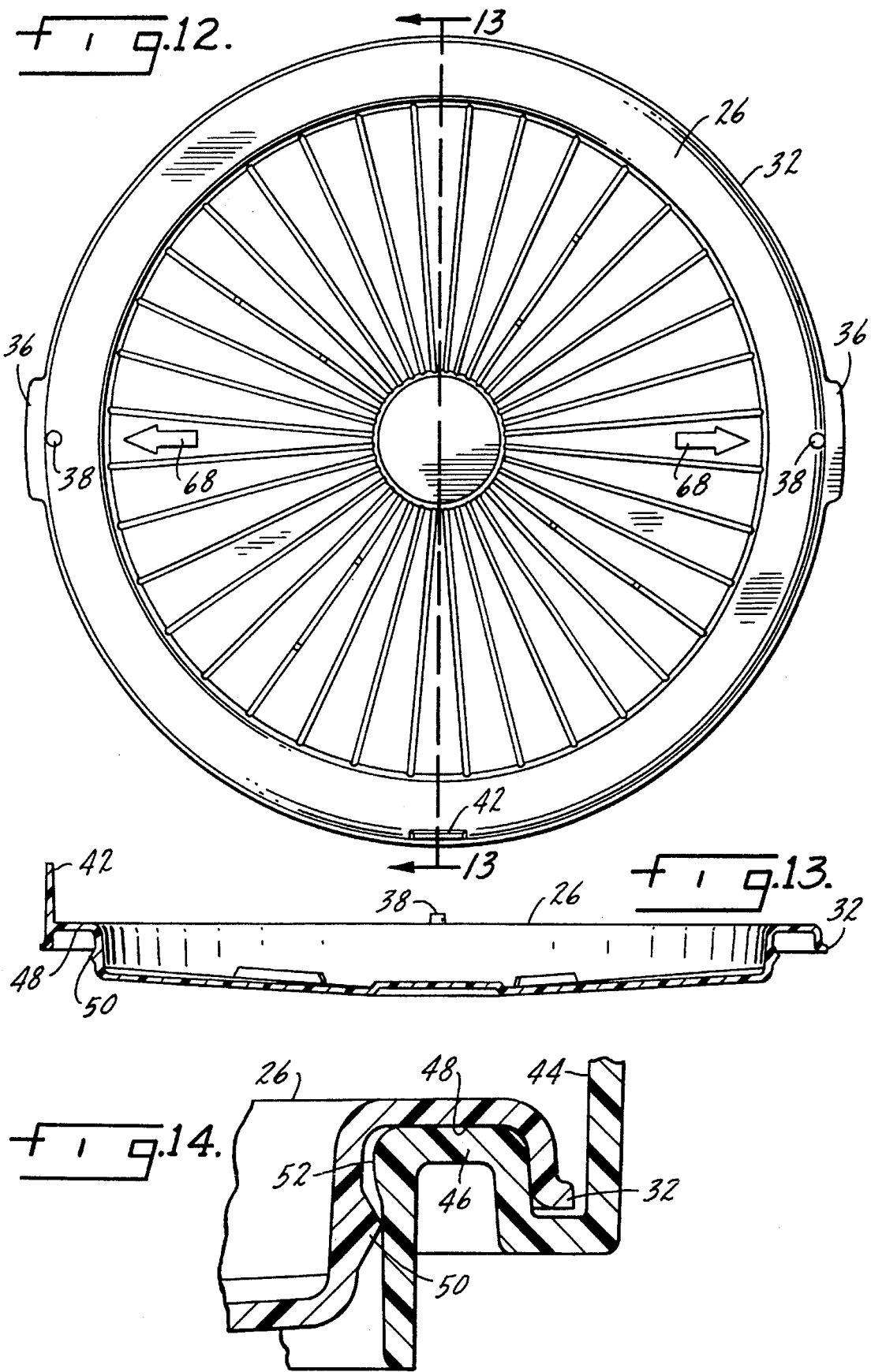

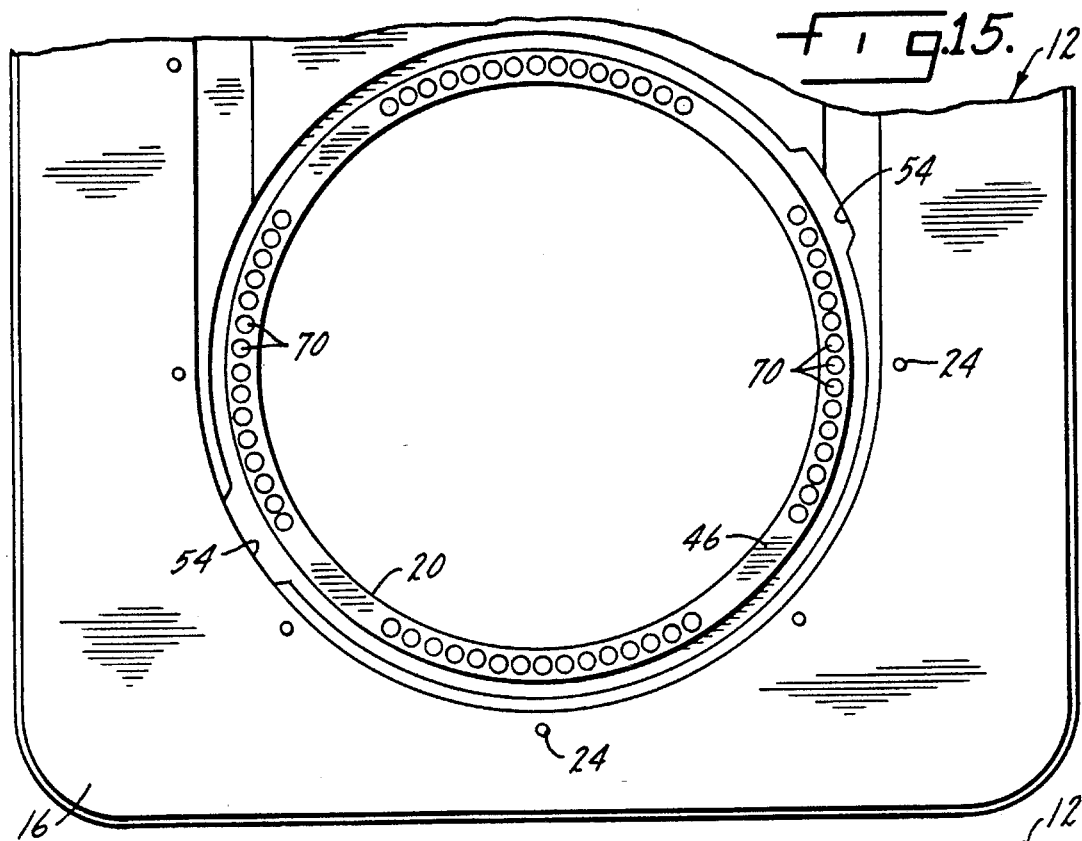
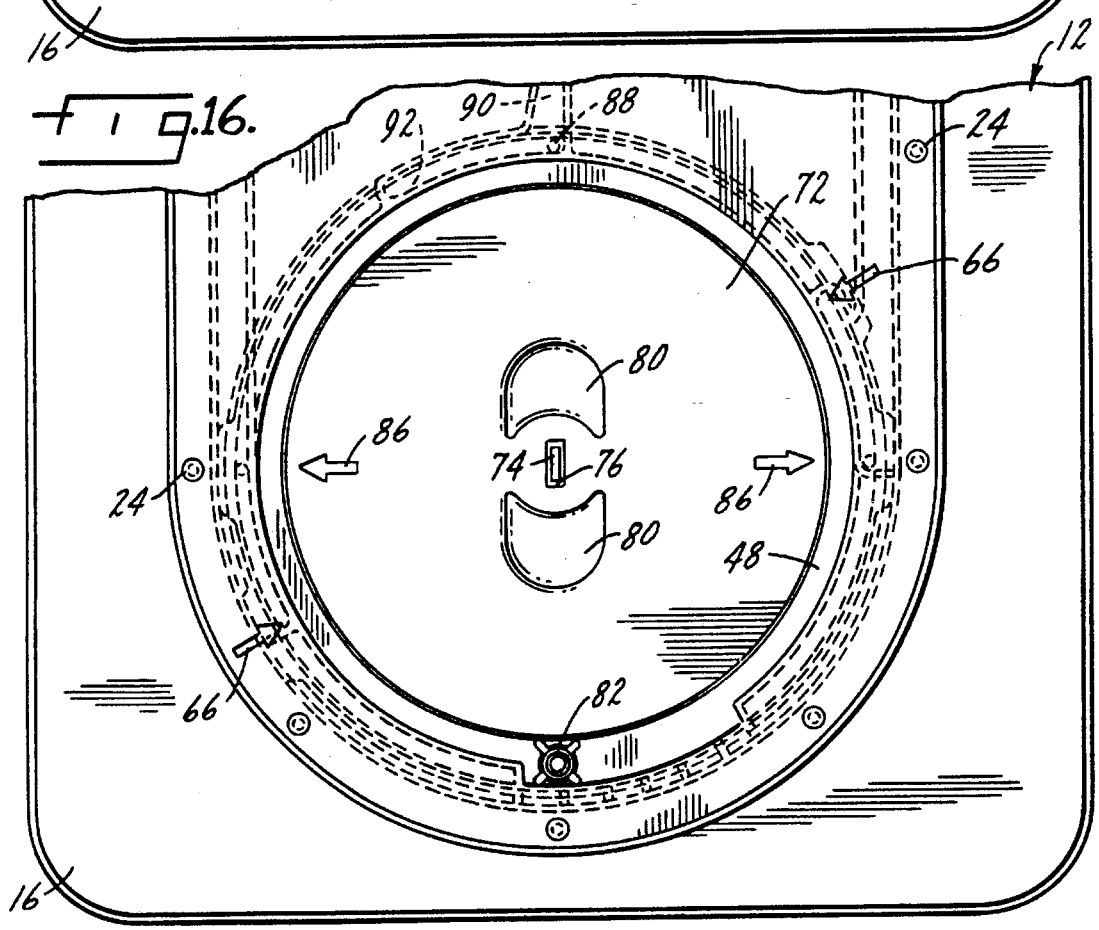

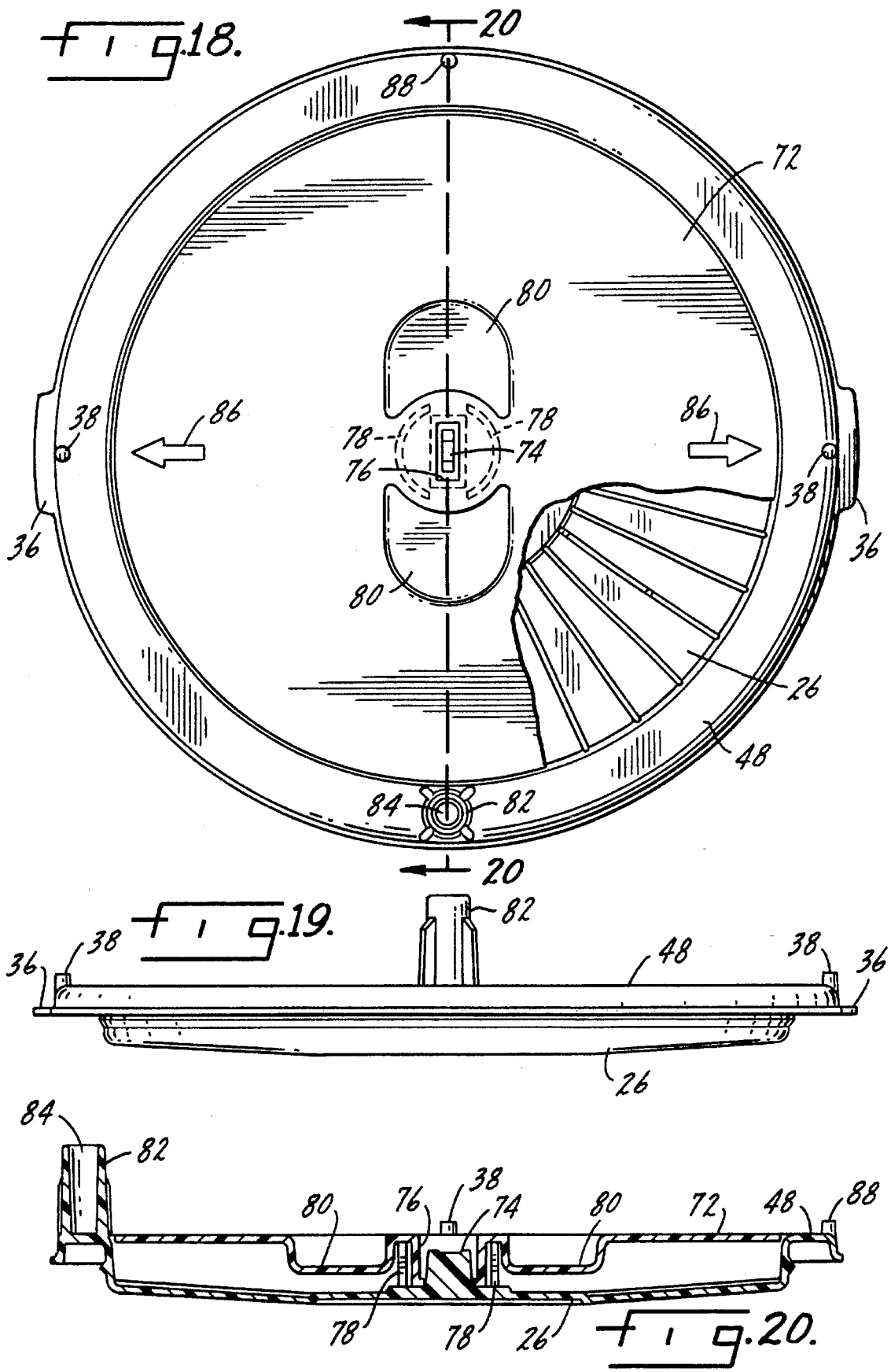

DISPOSAL CONTAINER WITH LOCKING CLOSURE AND INDICATOR TO PROVIDE VISUAL INDICATION OF LOCKING OF CLOSURE

RELATED APPLICATION

This application is a continuation-in-part of U.S. patent application Ser. No. 08/131,652, filed Oct. 5, 1993, now U.S. Pat. No. 5,507,408.

BACKGROUND OF THE INVENTION

This invention relates to disposal containers, and more particularly to a disposal container having a slidable cover which, in an operative position, may be moved to-and-fro to expose an access aperture, and which in a locked orientation seals the access aperture from future use.

In hospitals and similar medical institutions, when contamination is of concern, it is critically important that contaminated waste be disposed of properly. With the prevention of spread of communicable diseases being a major priority, disposable, single use patient care products have become quite prevalent. Those products, once used, are contaminated and can readily transmit disease, infection or other undesirable conditions. Therefore, it is imperative that, once a container has been filled with dangerous medical waste, it be sealed so that access to the interior of the container cannot inadvertently occur.

SUMMARY OF THE INVENTION

The invention provides a disposal container having a cover which includes a lid having means for attachment of the lid to the container body. An access aperture is provided in the lid, and a closure is provided, shaped to overlay the access aperture. Means is provided for positioning the closure in an operative position at a first elevation relative to the lid such that the closure is translatable from a temporarily closed orientation over the access aperture to an opened orientation. The opened orientation is such that at least a portion of the access aperture is exposed to permit passage through the access aperture. Means is provided for locking the closure at the access aperture at a second elevation relative to the lid in order to prevent passage through the access aperture and leakage from the aperture.

In accordance with the preferred form of the invention, the cover includes a hood extending over at least part of the lid, with the closure being located and slidable between the lid and the hood. The hood includes an opening in registration with the access aperture. The opening is generally the same in size as the access aperture.

The means for positioning the closure includes at least one guideway in the closure, with the closure including means intersecting the guideway to facilitate translation of the closure. Preferably, a pair of guideways is provided, each guideway comprising a channel in the hood extending from an opposite side of the access aperture. The means intersecting each guideway comprises an upstanding knob on the closure engaging each of the channels.

The closure includes a circumferential peripheral flange, and the lid includes opposite parallel ledges spaced such that the flange engages and is slidable upon the ledges. The ledges are provided to orient the closure at the first elevation.

For locking the closure, included is a pair of opposite tabs extending outwardly from the closure. A locking cavity is formed in the lid proximate the access aperture, the cavity having a sill engaged by the tabs for support of and translation of the closure at the first elevation. The cavity includes a pair of opposite recesses in the sill, the recesses being formed to accommodate the tabs for a vertical change of elevation of the closure from the first elevation to the second elevation. During translation, the closure is inhibited from rotation from the operative position except when the closure is in the temporarily closed orientation. Preferably, the recesses are circumferentially offset from the tabs when the closure is in the operative position, so that the tabs cannot engage the recesses except when the closure is purposely rotated in the closed orientation.

Means is provided for retaining the closure at the second elevation when locked. That means for retaining comprises an annular rim formed in the locking cavity and a corresponding peripheral channel formed in the closure. Means is provided for securing the channel to the rim, that means comprising a first annular protrusion in the channel and a second annular protrusion in the rim. The protrusions interengage when the closure is pushed downwardly to the second elevation.

In accordance with one form of the invention, there is means at the second elevation to provide a visual indication when the closure is located at the second elevation. In this form of the invention, the peripheral channel of the closure is translucent, and the annular rim adjacent the access aperture includes a series of markings. The markings are substantially invisible through the channel when the closure is at the first elevation and are visible through the channel when the closure is located at the second elevation. The markings are regularly spaced on the rim and preferably are dark in color to readily appear through the channel when the closure is located at the second elevation.

A protective disk is preferably located on the closure but spaced from the closure. In this form of the invention, the closure includes an upstanding post and the disk includes a depressed central aperture, the post being captured in the aperture. Means is also provided for supporting the disk above the closure, this means comprising at least one pedestal located centrally on the closure and supporting the disk thereabove.

The disk also includes a rotation aid to facilitate rotation of the disk, and therefore the closure, when the closure is fully closed. The rotation aid comprises a pair of spaced finger depressions in the disk.

In this form of the invention, the handle is more substantial and protrudes upwardly from the closure. The handle includes a central attachment socket for connection to a closure opening device.

In use, the closure normally is slid to-and-fro at the first elevation in order to provide or temporarily prevent access to the access aperture. When it is desired to permanently lock the closure in place, the closure is located at the access aperture. It is then relocated to align the tabs on the closure with the corresponding recesses in the lid. The closure is then depressed to the second elevation while engaging the annular channel of the closure with the annular rim formed about the access aperture. Preferably, the process of relocating includes rotating the closure relative to the lid when the closure is located over the access aperture. When the closure has been depressed, it is locked in place with the annular protrusion in the channel being oriented beneath the annular protrusion on the rim.

BRIEF DESCRIPTION OF THE DRAWINGS

The invention is described in greater detail in the following description of an example embodying the best mode of the invention, taken in conjunction with the drawing figures, in which:

FIG. 3 is an elevational view of a container according to the invention, with the bottom of the container being broken away to eliminate unnecessary detail, FIG. 4 is a cross-sectional view taken along lines 4—4 of FIG. 1, with the hood not being permanently heat staked in place, FIG. 5 is an enlarged cross-sectional view taken along lines 5—5 of FIG. 1, but without the hood being shown, FIG. 6 is an enlarged cross-sectional view taken along lines 6—6 of FIG. 1, FIG. 7 is an enlarged cross-section view taken along lines 7—7 of FIG. 2, FIG. 8 is a cross-sectional view similar to that of FIG. 7, but with the closure shown rotated and depressed into the locked position, FIG. 9 is a bottom plan view of the hood of the cover of the disposal container according to the invention, FIG. 10 is an enlarged cross-sectional view, shown in an upright orientation, taken along lines 10—10 of FIG. 9, FIG. 11 is an enlarged cross-sectional illustration, shown in an upright orientation, taken along lines 11—11 of FIG. 9, FIG. 12 is an enlarged top plan view of a closure according to the invention, FIG. 13 is a cross-sectional illustration taken along lines 13—13 of FIG. 12, FIG. 14 is a greatly enlarged cross-sectional illustration of the interengagement of the closure in the cavity about the access aperture in the lid, when locked in place, FIG. 15 is a top plan view of a portion of the lid of a second form of the invention, with the closure and hood removed, and showing visual indication dots, FIG. 16 is a view similar to FIG. 15, but with the hood in place and illustrating a second form of closure according to the invention, including a protective disk, FIG. 18 is an enlarged top plan view of the closure illustrated in FIG. 16, with a portion broken away to illustrate detail, FIG. 19 is a side elevational view of the closure of FIG. 18, and FIG. 20 is a cross sectional view taken along lines 20—20 of FIG. 18.

DESCRIPTION OF AN EXAMPLE EMBODYING THE BEST MODE OF THE INVENTION

Figure 1:
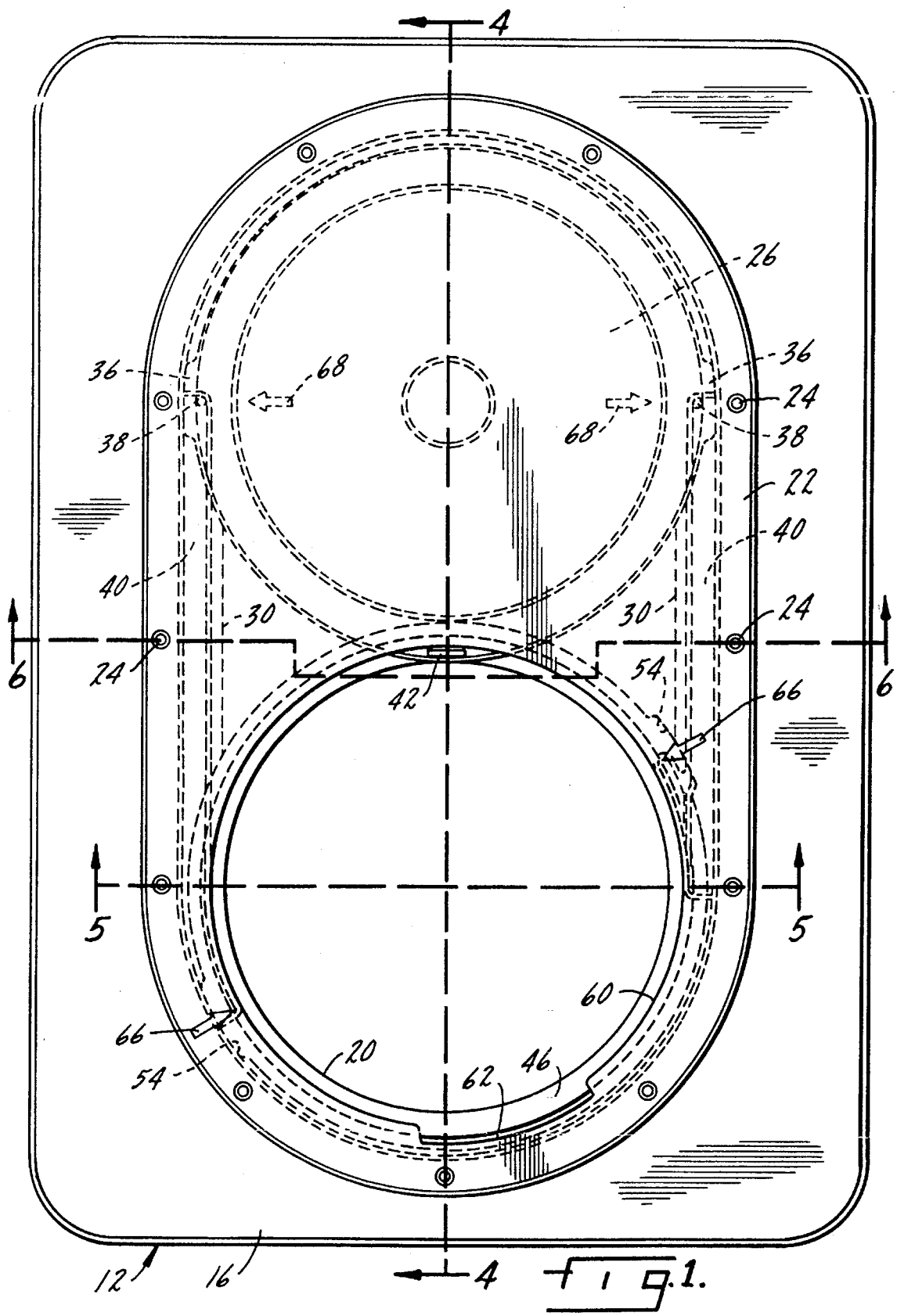
FIG. 1 is a top plan view of a disposal container according to the invention, with the closure being fully retracted within the cover to expose the access aperture.

A disposal container according to the invention is shown generally at 10 in FIG. 3. The disposal container 10 comprises two basic portions, a cover 12 and a container body 14. The container body 14 may be of any depth desired, and therefore only a portion of the container body 14 is illustrated. Of course, the container body 14 is generally unitary with an open top, where the cover 12 is applied.

The cover 12 includes a lid 16. The lid 16 is shaped for attachment to the container body 14, and may be attached in a conventional fashion. For example, the lid 16 may include an in-turned flange 18 (FIG. 6) which engages an outwardly extending lip (not illustrated) on the top of the container body 14. The lid 16 may also include a series of buttresses (not illustrated) to lock the lip of the container body 14 within the flange 18. This connection mechanism is conventional, and any other type of connection can be employed as well. Also, in some instances, the lid 16 can be an integral extension of the container body 14.

The lid 16 includes an access aperture 20 therein. As shown, the access aperture 20 is generally circular, and is sized as desired to allow access to the interior of the disposal container 10.

A hood 22 is provided, being appropriately affixed to the lid 16, such as by heat staking a series of upstanding knobs 24 extending upwardly from the lid 16 and passing through appropriate apertures in the hood 22. Other detail of the hood 22 is described in greater detail below.

A closure 26 is sandwiched between the hood 22 and the lid 16. The closure 26 is shaped to cover the access aperture 20, as explained in greater detail below.

The lid 16 includes a central depressed area 28 to accommodate sliding of the closure 26 beneath the hood 22. The depressed area 28 includes opposite parallel ledges 30, actually in the form of a continuous flange extending about the depressed area 28. The closure 26 includes a corresponding peripheral flange 32 which is seated upon the ledges 30 as the closure 26 is slid to-and-fro beneath the hood 22.

In the vicinity of the aperture 20, the ledges 30 diminish in size, becoming a much smaller sill 34. The sills 34 are spaced apart a distance greater than the diameter of the closure 26 as defined by the peripheral flange 32. Thus, the closure 26 normally would not be supported when extending above the access aperture 20. However, the closure 26 is also provided with a pair of opposite tabs 36 which extend outwardly from the flange 32, and are shaped to ride upon the narrow sills 34. Thus, in normal operation, the closure 26 is slid to-and-fro at one elevation relative to the lid 16, with either the flange 32 being seated upon and riding upon the ledges 30, or with the extending tabs 36 being seated upon and riding upon the opposite sills 34.

In order to retain the closure 26 in a proper orientation for normal sliding operation as explained above, the closure 26 includes a pair of upstanding knobs 38. The knobs 38 intersect and extend into guideways in the form of opposite channels 40 formed in the underside of the hood 22. The opposite knobs 38, extending into the opposite channels 40, align the closure 26 in the normal orientation illustrated as the closure 26 is slid back and forth beneath the hood 22. To that end, the closure 26 preferably is provided with an upstanding ear or handle 42 which forms a handle for operation of the closure 26.

In addition to normal operation of the closure 26 to temporarily cover and uncover the entirety or any portion of the access aperture 20, the closure 26 and access aperture 20 are also formed so that the closure 26 can be permanently locked in place. To that end, the lid 16 includes a locking cavity 44 extending beneath the opposite sills 34 with an annular rim 46 extending about the access aperture 20. The closure 26 includes a corresponding peripheral channel 48 which, when the closure 26 is depressed downwardly as shown in FIGS. 8 and 14, seats on the annular rim 46. To enhance that seating and secure the closure 26 at the second elevation illustrated in FIG. 8, the peripheral channel 48 includes a first annular protrusion 50 and the annular rim 46 includes a second annular protrusion 52. As illustrated, the first annular protrusion 50 seats below the second annular protrusion 52 when the closure 26 is depressed to the second elevation, thus enhancing the interengagement of the peripheral channel 48 on the annular rim 46, and therefore the locking of the closure 26 at the second elevation.

As explained above, because of the orientation of the closure 26 with the tabs 36 inhibiting depression of the closure 26 to the second, lower elevation, the closure 26 normally cannot be locked at that lower elevation. The upstanding knobs 38 extending in the channels 40 assure this relationship. In order for the closure 26 to be depressed to the lower, second elevation, it must be rotated until the tabs 36 engage a pair of opposite recesses 54 extending in the sills 34. To permit this rotation, one of the channels 40 includes a curved extension 56. The other of the channels 40 includes a side track 58. The extension 56 and side track 58 accommodate the upstanding knobs 38 when rotation of the closure 26 is desired.

In addition, to allow access into the interior of the disposal container 10, the hood 22 includes an opening 60. The opening 60 is generally round, and is somewhat smaller in diameter than the closure 26, thus assuring that the closure 26 cannot escape. A notch 62 is formed along one peripheral edge of the opening 60 in order to accommodate the handle 42 when the closure 26 is rotated to align the tabs 36 with the recesses 54. When so aligned, the closure 26 can then be pushed downwardly, depressing it to the second orientation and locking it in place. Because the handle 42 is depressed below the top surface of the cover 12 (see FIG. 8), it is quite difficult, if not impossible, to remove the closure 26 when locked in place.

The closure 26 must be purposefully rotated when fully closed over the access aperture 20 in order to initiate final locking of the closure 26. To assure that the closure 26 is not inadvertently rotated, the side track 58 is provided with an entry detent 64 which engages an upstanding knob 38. The upstanding knob 38 must be forced past the entry detent 64 into the side track 58 when rotating the closure 26. Thus, the entry detent 64 provides some resistance to initial rotation of the closure 26 from the normal orientation.

As illustrated in the drawings, the lid 16 can be provided with a pair of alignment arrows 66 in registration with the recesses 54. Similarly, the closure 26 can be provided with a pair of alignment arrows 68 in registration with the extending tabs 36. When the arrows 66 and 68 are aligned, the closure 26 has been sufficiently rotated so that it can be depressed and locked in place as shown in FIG. 8.

Figure 2:
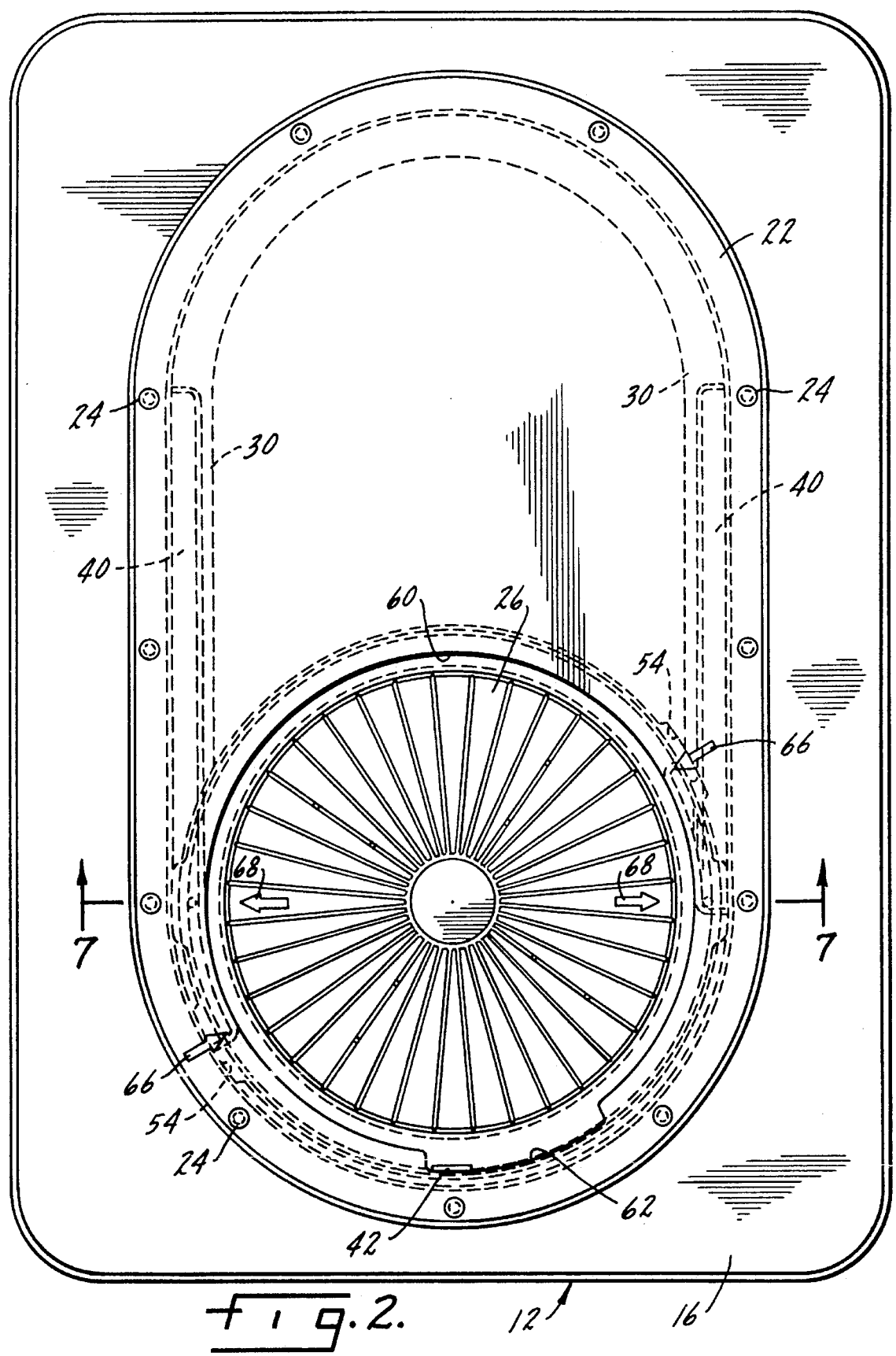
FIG. 2 is view similar to FIG. 1, but with the closure returned to cover the access aperture.
Figure 17:
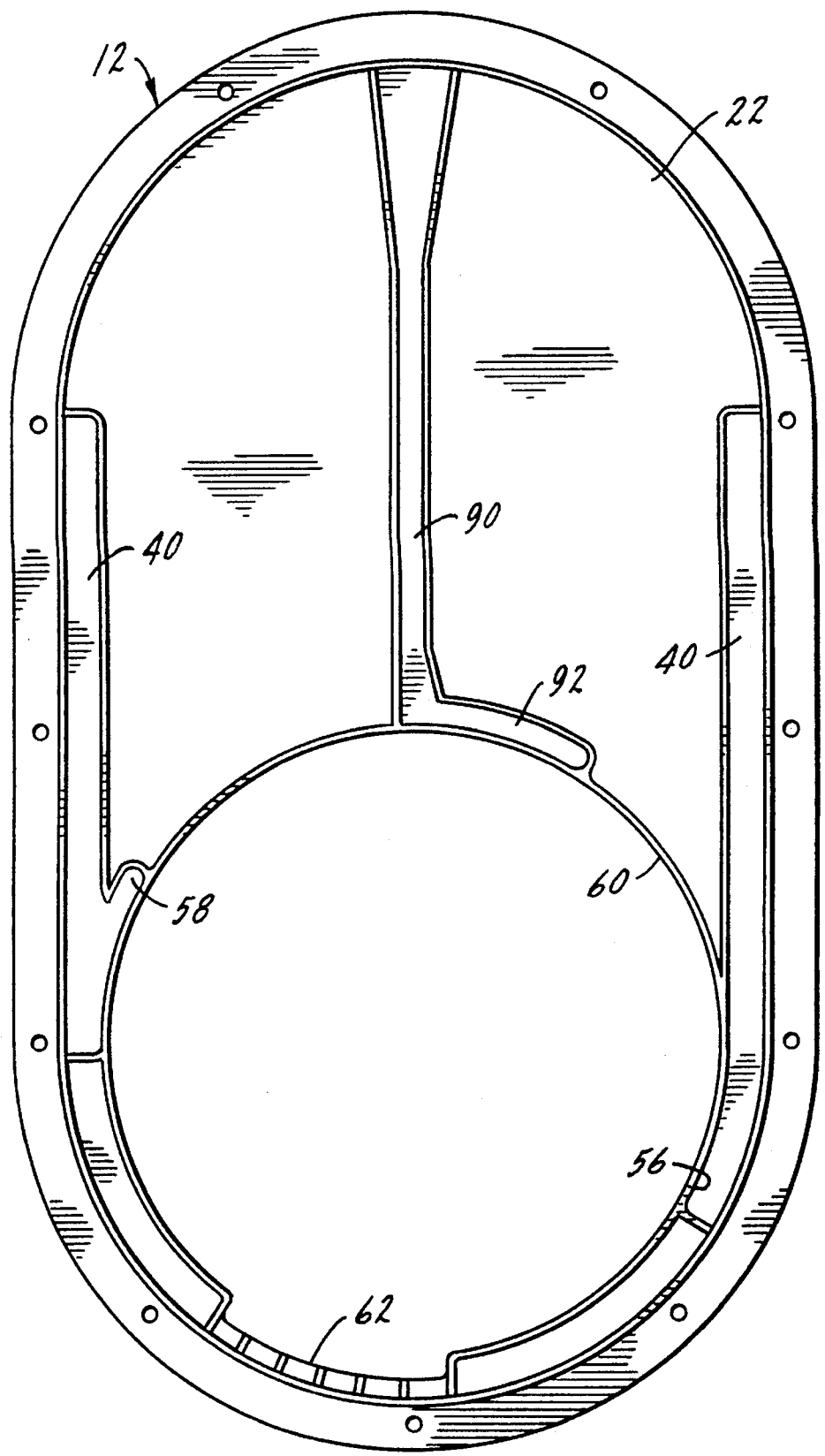
FIG. 17 is a bottom plan view of the hood of the form of the disposal container illustrated in FIG. 16.

To reiterate the operation of the disposal container 10, normally the closure 26, which is captured beneath the hood 22, is slid to-and-fro with the peripheral flange 32 riding on the ledges 30 and/or the tabs 36 riding on the sill 34. When final locking of the disposal container 10 is desired, the closure 26 is fully closed as shown in FIG. 2, with the handle 42 seated in the notch 62. The closure 26 is then rotated (counterclockwise in FIG. 2) until the arrows 66 and 68 align. At that position, the tabs 36 extend above the recesses 54, and the closure 26 can then be pushed downwardly to the second elevation illustrated in FIG. 8. When so-depressed, the closure 26 is locked in place by virtue of the peripheral channel 48 seating on the annular rim 46, with the annular protrusions 50 and 52 being interengaged.

A second form of the invention is illustrated beginning in FIG. 15. Like elements of the invention retain the same reference numerals and functions as described above, and are not described further.

In this form of the invention, as shown in FIG. 15, the annular rim 46 is provided with a series of visual indicators in the form of markings 70 which are regularly spaced on the rim 46. The markings preferably are dark in color to be more readily visible, and also are shown as a series of round dots, although other types of markings can be used. In this form of the invention, the channel 48 of the closure 26 is translucent, so that when the closure 26 is in the first elevation, the markings 70 are substantially invisible. However, when the closure 26 is rotated and depressed to the second orientation, the markings 70 appear clearly through the channel 46 to indicate that the closure 26 has been properly depressed to the second elevation. If only some of the markings 70 are visible, and others are only partially visible or invisible, that is an indication that the closure 26 has not been properly depressed to the second elevation.

As illustrated in FIG. 16 and FIGS. 18 through 20, the closure 26 also includes a protective disk 72 mounted on the closure 26. As best shown in FIG. 20, the disk 72 is spaced from the closure 26 to provide a gap and therefore provide protection to the user in case a needle or other sharp object within the container should accidentally pierce the closure 26.

The closure 26 includes an upstanding post 74 and the disk 72 includes a depressed central aperture 76, with the post 74 being captured in the aperture 76. To further support the disk 72 above the closure 26, a pair of pedestals 78 are located centrally on the closure 26, spaced about the upstanding post 74. As shown in FIG. 20, the pedestals 78 bear on the underside of the disk 72 to support the disk above the closure 26.

To aid in rotation of the closure 26 when desired, the disk 72 includes a pair of spaced fingered depressions 80. As explained above, the finger depressions 80 can be used to rotate the closure 26 only when the closure 26 is fully closed over the access aperture 20.

As illustrated, the closure of this form of the invention also includes a handle 82 to facilitate translation of the closure 26 between the opened and closed positions. The handle 82 includes a central attachment socket 84 so that the closure can be attached to another device for remote opening and closing of the closure 26. A rod or similar structure would fit in the socket 84.

Similar to the first form of the invention, the disk 72 includes a pair of alignment arrows 86 which are alignable with the alignment arrows 66 when the closure 26 is rotated. Other means of alignment other than the various arrows can be employed, as would be evident to one skilled in the art.

In this form of the invention, for increased stabilization of the closure 26, preferably the closure 26 includes a central knob 88 in addition to the two knobs 38. The knob 88 is guided in a channel 90 formed on the underside of the hood 22, and when the closure 26 is rotated, the knob 88 is guided in a side track 92.

Various changes can be made to the invention without departing from the spirit thereof or scope of the following claims.

What is claimed is:

1. A cover for a container, comprising
   a. a lid, said lid including means for attachment of said lid to a container body,
   b. an access aperture in said lid,
   c. a closure shaped to overlay said access aperture,
   d. means for positioning said closure in an operative position at a first elevation relative to said lid with said lid being translatable at said first elevation from a temporarily closed orientation over said access aperture to an opened orientation such that at least a portion of said access aperture is expected to permit passage through said access aperture.

e. means for facilitating depressing of said closure at said access aperture from said first elevation to a second elevation relative to said lid, and f. means at said second elevation and visible only when said closure is at said second elevation to provide a visual indication when said closure is located at said second elevation.

2. A cover according to claim 1 in which said closure includes a translucent peripheral channel and said access aperture includes an annular rim corresponding to said channel, and in which said means to provide a visual indication comprises a series of markings on said rim, said markings being substantially invisible through said channel when said closure is at said first elevation and being visible through said channel when said closure is located at said second elevation.

3. A cover according to claim 2 in which said markings are regularly spaced on said rim.

4. A cover according to claim 2 in which said markings are dark in color.

5. A cover according to claim 1 including a protective disk on said closure, said disk being spaced from said closure.

6. A cover according to claim 5 in which said closure includes an upstanding post and said disk includes a depressed central aperture, said post being captured in said aperture.

7. A cover according to claim 5 in which said closure further includes means supporting said disk above said closure.

8. A cover according to claim 7 in which said supporting means comprises at least one pedestal located centrally on said closure.

9. A cover according to claim 5 in which said closure is rotatable and in which said disk includes a rotation lid.

10. A cover according to claim 9 in which said rotation aid comprises a pair of spaced finger depressions in said disk.

11. A cover according to claim 1 including an upstanding handle on said closure for manipulation thereof.

12. A cover according to claim 11 in which said handle includes a central attachment socket.

13. A cover for a container, comprising a. a lid, said lid including means for attachment of said lid to a container body, b. an access aperture in said lid, c. a closure shaped to overlay said access aperture, d. means for positioning said closure in an operative position at a first elevation relative to said lid with said lid being translatable at said first elevation from a temporarily closed orientation over said access aperture to an opened orientation such that at least a portion of said access aperture is exposed to permit passage through said access aperture, e. means for facilitating depressing of said closure at said access aperture from said first elevation to a second elevation relative to said lid, and f. a protective disk on said closure, said disk having a portion spaced from said closure creating a space between said closure and said disk such that if said closure is penetrated by a sharp object, said disk can remain unpenetrated.

14. A cover according to claim 13 in which said closure includes an upstanding post and said disk includes a depressed central aperture, said post being captured in said aperture.

15. A cover according to claim 13 in which said closure further includes means supporting said disk above said closure.

16. A cover according to claim 15 in which said supporting means comprises at least one pedestal located centrally on said closure.

17. A cover according to claim 13 in which said closure is rotatable and in which said disk includes a rotation lid.

18. A cover according to claim 17 in which said rotation aid comprises a pair of spaced finger depressions in said disk.

19. A cover according to claim 13 including means at said second elevation to provide a visual indication when said closure is located at said second elevation.

20. A cover according to claim 19 in which said closure includes a translucent peripheral channel and said access aperture includes an annular rim corresponding to said channel, and in which said means to provide a visual indication comprises a series of markings on said rim, said markings being substantially invisible through said channel when said closure is at said first elevation and being visible through said channel when said closure is located at said second elevation.

* * * * *